United States Patent [19]

Adams et al.

[11] Patent Number: 5,312,443
[45] Date of Patent: May 17, 1994

[54] ARRHYTHMIA-DETECTION CRITERIA PROCESS FOR A CARDIOVERTER/DEFIBRILLATOR

[75] Inventors: Theodore P. Adams, Edina; Mark W. Kroll, Minnetonka; Charles G. Supino, Arden Hills, all of Minn.

[73] Assignee: Angeion Corporation, Plymouth, Minn.

[21] Appl. No.: 837,952

[22] Filed: Feb. 20, 1992

[51] Int. Cl.$^5$ .............................................. A61B 5/04
[52] U.S. Cl. ................................... 607/5; 128/705
[58] Field of Search ................... 128/419 D, 419 PG; 607/5, 6, 18, 19

[56] References Cited

U.S. PATENT DOCUMENTS

| | | | |
|---|---|---|---|
| 3,805,795 | 4/1974 | Denniston et al. | 128/419 D |
| 4,202,340 | 5/1980 | Langer et al. | 128/419 D |
| 4,475,551 | 10/1984 | Langer et al. | 128/419 D |
| 4,796,620 | 1/1989 | Imran | 128/706 |
| 4,865,036 | 9/1989 | Chirife | 128/419 D |
| 4,873,980 | 10/1989 | Schaldach | 128/419 PG |
| 4,880,005 | 11/1989 | Pless et al. | 128/419 PG |
| 4,905,697 | 3/1990 | Heggs et al. | 128/419 PG |
| 4,945,909 | 8/1990 | Fearnot et al. | 128/419 PG |
| 5,042,497 | 8/1991 | Shapland | 128/419 D X |
| 5,054,485 | 10/1991 | Cohen | 128/419 D |
| 5,097,831 | 3/1992 | Lekholm | 128/419 PG |

Primary Examiner—Lee S. Cohen
Assistant Examiner—Jeffrey R. Jastrzab
Attorney, Agent, or Firm—Patterson & Keough

[57] ABSTRACT

A major shortcoming in the prior art for detecting cardiac arrhythmias for the purpose of making an electrical intervention decision has been that each variable sensed was given in effect a "veto" over intervention on the basis of its own particular predetermined threshold value, and irrespective of the values of companion variables. The present invention overcomes this prior art problem by generating a function of relevant variables, and assigning a threshold value to the function. As a result, an individual variable can range widely for a positive intervention decision, depending upon the values of the companion variables. Thus, the intervention exploits features often described as those associated with fuzzy logic. The functions chosen for this purpose can be as one desires, with the choice depending upon the current state of advancing knowledge. Even further flexibility can be achieved by employing the principles of the neural net, wherein functional values can themselves be combined, with another threshold value assigned to the result of that combination, and so on.

18 Claims, 6 Drawing Sheets

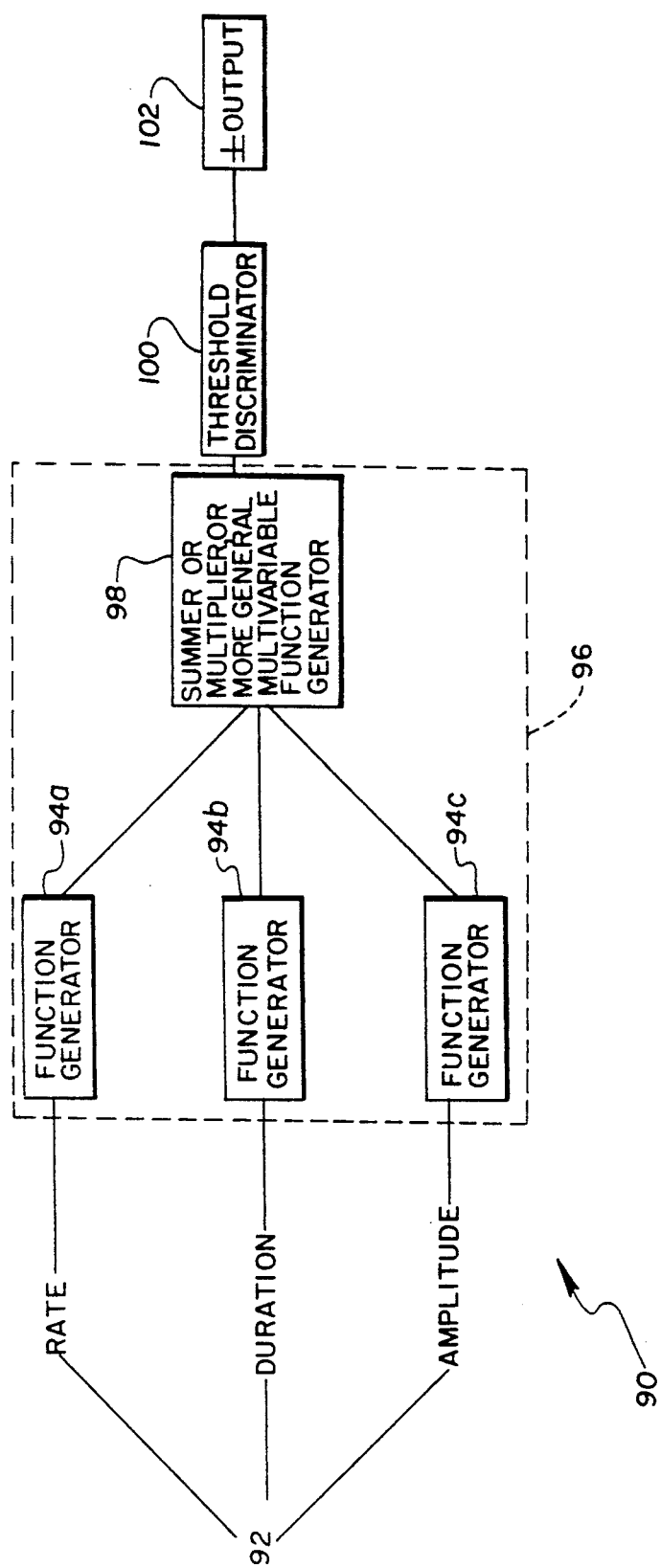

ARRHYTHMIA-DETECTION CRITERIA PROCESS FOR A CARDIOVERTER/DEFIBRILLATOR

BACKGROUND OF THE INVENTION

1. Field of the Invention

The present invention relates generally to detection methods for cardiac arrhythmias, and more particularly, to methods of improved accuracy for identifying the presence of conditions that can be ameliorated by antitachycardia pacing, by cardioversion shock, or by defibrillation shock.

2. Description of the Prior Art

Fibrillation is a chaotic and uncoordinated contraction of the ventricular myocardium. The heart can be caused to return to normal rhythm by the application of an energetic electrical shock, typically of the order of 10 joules. Cardioversion involves the application of a more modest shock, typically in the neighborhood of one joule, and is appropriate in the case of ventricular tachycardia. The heart in this condition has a high, but well-defined rate, but its contraction is not as well-coordinated as it is in the normal state, the condition of normal sinus rhythm. Furthermore, if the rate is high enough, pumping efficiency declines significantly. Ventricular tachycardia, still further, is sometimes a precursor of fibrillation.

When the heart races, but retains well-coordinated contractions, effective intervention is sometimes possible by applying a pacing signal of still higher rate that "takes over" from the tachycardia, and then returns the rate to the proper range. This treatment is appropriate when the rise in rate has not been too large.

Several prior-art tactics have been used to identify malfunctions such as these, in order to apply the appropriate electrical protocol. But these have left much to be desired in terms of accuracy and reliability. For example, a simple and common criterion for the application of a defibrillation shock is a pulse rate above 170 per minute. But such an elevated rate can and should result from exercise, to name one cause, the case of "sinus" tachycardia. Under such conditions, a "false positive" instruction to the defibrillator results from the sole use of the simplistic rate criterion, followed by the delivery of a painful and possibly hazardous shock to the patient.

More sophisticated systems monitor more than one variable. For example, rate of change of the pulse rate is sometimes observed, to detect a rapid "jump" in heart rate. In variations on this method, one can monitor rate acceleration, or the magnitude of the rate change within a given interval. More general approaches are covered in the discussion below under the term "onset". Another criterion is duration of high heart rate, measured in the number of consecutive cycles above a specified rate. Other options examine the correlation between electrical pulses and separate signals derived from a mechanical sensor of some description.

Yet another option observes a quantity that is related to the waveform shape of the signal from the heart. For example, the ratio of the average absolute value of the signal voltage to the peak absolute voltage is small during normal sinus rhythm, because the signal departs from near zero for a relatively small fraction of the cycle. In the chaotic signal from a fibrillating heart it is nonzero much more of the time. This kind of absolute-amplitude observation is included below under the brief term "absolute-amplitude ratio" (AAR). The probability distribution function (PDF) is a useful detection approach involving waveform shape. A further criterion is signal amplitude. Amplitude declines significantly during fibrillation. Still further, one can observe blood pressure, blood pH, and other physiological-variable values. Finally, there is the stability criterion. Here the rate variation can suggest an exercise-related change in normal sinus rhythm, or the chaotic behavior connected with ventricular fibrillation, but rules out the middle ground of ventricular tachycardia.

A number of U.S. Patents deal with the detection of ventricular arrhythmias by using observations of more than one variable. The inventors, patents, dates, and variables can be summarized as follows:

Dennisten and Davis, U.S. Pat. No. 3,805,795, 1974, electrical and mechanical.

Langer and Heilman, U.S. Pat. No. 4,475,551, 1984, rate and PDF.

Imran, U.S. Pat. No. 4,796,620, 1989, rate and onset.

Chirife, U.S. Pat. No. 4,865,036, 1989, rate and mechanical.

Pless and Sweeney, U.S. Pat. No. 4,880,005, 1989, rate and stability.

In these multi-variable systems, it is standard practice to set a threshold level for each variable that, when exceeded, contributes a positive "vote" to the decision. These discrete criteria are combined in a logical AND function, thus requiring a unanimous vote, and a particular electrical treatment is initiated by the positive AND output.

To illustrate the shortcomings of such a system and also a single-variable threshold-method system, let us take a two-variable example. The same kind of example is useful to illustrate the advantages of the present invention, as described in the following section. The principles involved in more complex systems will be evident as extension of this example. Suppose that ventricular tachycardia is to be detected and at most two variables are to be monitored, heart rate and duration of the elevated rate.

As the single-variable example, let us take the case of pulse-rate monitoring only. This case is illustrated in FIG. 1A, where the x axis is labeled "rate". The y axis is present also, and is labeled "duration", but is included only to relate this case to subsequent cases. The standard technique chooses a discrete threshold $r^*$, and triggers electrical therapy when the rate exceeds $r^*$. It follows, then, that any pulse rate falling in the shaded region will produce a positive indication. The obvious problem with this simplistic method is that even a condition represented by the point with the coordinates $(r_1, d_1)$ will trigger therapeutic response in spite of the fact that the high rate was very fleeting.

Moving then to the two-variable method, we can see that such a false positive is ruled out by "ANDING" the pair of variables. It is now necessary to have $r > r^*$, and $d > d^*$ simultaneously in order to trigger electrical response. This situation is illustrated graphically in FIG. 1B, and the now more restricted shaded area represents the locus of points that trigger the system. Thus, it follows that the false-positive condition represented by the point $(r_1, d_1)$ does not cause triggering. This is not the end of the story, however. Note that the condition represented by the point $(r_2, d_2)$ will not trigger the system either, but certainly represents a case of tachycardia because the rate is high (though slightly below threshold) for a very long time. The system design of the present invention eliminates this shortcoming, as well as that associated with a point such as ($r_1$, $d_1$).

SUMMARY OF THE INVENTION

The present invention removes the shortcomings of the prior art by setting a threshold value for a function of the relevant variables, rather than for the variables individually. This permits an individual variable to range widely and continuously for a given positive decision, depending upon the respective values of the companion variables. Thus, the present invention eliminates a major problem of the prior art, the ability of each variable in effect to veto a positive decision, no matter how extreme the values of other variables. The chosen function of the relevant variables may be linear or nonlinear, as desired. Furthermore, one may also weight the individual variables with total discretion, and to refine these weights progressively as knowledge and the art advance, and as methods for distinguishing among the various tachycardias are improved.

To illustrate the present invention, let us continue with the two-variable example, where these variables are rate r and duration d. Let the combined reference values of $r\cdot = 180/s$, and $d\cdot = 30$ (repeated cycles at the elevated rate, a number, and hence a dimensionless quantity) define one point on the functional curve beyond which tachycardia will be declared. Let the first function chosen be nonlinear, simply the product of variables, so that tachycardia is diagnosed when:

$$f(r, d) = rd > (180/s)(30) = 5400/s \qquad \text{Eq. 1}$$

For clarity and convenience, however, it is worthwhile to normalize the variables r and d, which renders the threshold value dimensionless and in the present case equal to unity when the reference values are used for normalization:

$$R \equiv \frac{r}{r_0} = \frac{r}{180/s} \qquad \text{Eq. 2}$$

$$D \equiv \frac{d}{d_0} = \frac{d}{30} \qquad \text{Eq. 3}$$

Using these definitions, tachycardia will be diagnosed when:

$$f(R, D) = RD > 1 \qquad \text{Eq. 4}$$

The threshold function $RD = 1$ is plotted in FIG. 2A. It is clear that the hyperbolic curve presented there constitutes the dividing line between intervention (the shaded area) and nonintervention (the unshaded area) as also indicated in FIG. 2A. Note that this functional criterion improves upon the prior art illustrated in FIG. 1B because the conditions represented there by the points with coordinates ($r_1$,$d_1$) and ($r_2$,$d_2$) now result in nonintervention and intervention, respectively, as they should.

The principle of this example can be extended to three variables readily. This converts the threshold curve into a threshold surface, hyperbolic once more, and easily visualized in three dimensions. Extension to four variables cannot be graphically illustrated with ease, but leads to a situation that can be grasped conceptually with no difficulty.

In any of these cases, as well as those involving still more variables, weights can be easily applied to the several variables by employing exponents of a chosen power for each. This situation is illustrated by a plot of the threshold function in FIG. 2B for a case where the exponents are 2 and 1, respectively. In this example, one opts for intervention when:

$$f(R, D) = R^2 D > 1 \qquad \text{Eq. 4}$$

It is, of course, equally easy to use fractional exponents if desired.

Turning now to a linear example, let us continue with the same reference values, $r\cdot = 180/s$, and $d\cdot = 30$. Letting the corresponding coordinates define a point on the threshold curve once more, we can write the threshold function this time for the simplest case as:

$$f(R, D) = R + D = 2 \qquad \text{Eq. 5}$$

This curve is plotted in FIG. 3A. Weights can be applied to the variables by simply placing a factor on each term. When these are 1.2 and 0.8, respectively, the resulting equation is:

$$f(R, D) = (1.2)R + (0.8)D = 2 \qquad \text{Eq. 6}$$

and the resulting threshold curve is as illustrated in FIG. 3B. The linear examples of FIG. 3A (Eq. 5) and FIG. 3B (Eq. 6) and the nonlinear example of FIG. 4A (Eq. 7) can serve usefully in intermediate ranges, but it is of course clear that the function must be cropped before touching either axis. That is, for example, a tachycardia of zero duration does not warrant response.

A further nonlinear example is provided by writing a sum of terms, any of which can be assigned an exponent for weighting as desired. For the particular example illustrated in FIG. 4A, where the exponents are 2 and 1, respectively, the threshold function is:

$$f(R, D) = R^2 + D = 2 \qquad \text{Eq. 7}$$

As a further nonlinear example, the choice of $-2$ and $-1$ for the respective exponents lead to the curve plotted in FIG. 4B, for which the threshold function is:

$$f(R,D) = R^{-2} + D^{-1} = 2 \qquad \text{Eq. 8}$$

Implementation of the criteria illustrated in FIGS. 2A through 4B will be achieved by means of a circuit module illustrated in black-box fashion in FIG. 5A. In this example, a single sensor delivers digital information on rate, duration and amplitude, and the signal in each channel is fed into a dedicated function generator. The resulting three output signals are then combined in another function generator that is capable of summing them, multiplying them, or performing some other more complex functional manipulation. Next, two or more such signals are fed into a circuit that generates a digital signal giving the value of a chosen multivariable function. For example, in the three-variable analogy to the two-variable case depicted in FIG. 2A, the product of the three variable values will be produced. And finally a discriminator circuit will determine whether the functional value is greater or less than a chosen threshold value, the criterion in the present invention. A positive result calls for intervention to deal with a tachycardia, and negative value, for no intervention.

It is, of course, possible to choose more complicated functions and fractional powers, as new findings justify their use. But this does not exhaust the options for treating complex interrelationships among the cardiac variables, or among functions of these variables. A further possibility is to employ the principles of the neural network, or neural net. One example is presented in FIG. 5B, wherein three variables fed into each of three modules similar to that enclosed by a dashed line of FIG. 5A, identified in FIG. 5B as $M_1$, $M_2$, and $M_3$. The values of the three resulting functions are then fed into another function generator, one that determines the value of a prescribed function of its three input functions, and that also performs the discrimination procedure.

On significant aspect and feature of the present is a criterion for cardiac arrhythmia-correcting electrical intervention that is a particular value of a function of at least two cardiac variables.

Another significant aspect and feature of the present invention is a criterion for cardiac arrhythmia-correcting electrical intervention that is a particular value of a product of at least two cardiac variables.

Still another significant aspect and feature of the present invention is a criterion for cardiac arrhythmia-correcting electrical intervention that is a particular value of a product of at least two cardiac variables with a weight in the form of an exponent of a power associated with each variable.

Yet another significant aspect and feature of the present invention is a criterion for cardiac arrhythmia-correcting electrical intervention that is a particular value of a sum of at least two cardiac variables.

Another significant aspect and feature of the present invention is a criterion for cardiac arrhythmia-correcting electrical intervention that is a particular value of a sum of at least two cardiac variables with a weight in the form of a multiplicative factor associated with each variable.

Still another significant aspect and feature of the present invention is a criterion for cardiac arrhythmia-correcting electrical intervention that is a particular value of a sum of at least two terms incorporating cardiac variables with weights in the form of an exponent of a power associated with each variable.

Yet another significant aspect and feature of the present invention is the use of a particular value of a function of multiple cardiac variables, such as various combinations of rate, onset, duration, correlations, absolute-amplitude ratio (AAR), stability, and physiological-variable values such as blood pressure and blood pH, to generate a criterion for cardiac arrhythmia-correcting electrical intervention.

Another significant aspect and feature of the present invention is the use of fuzzy logic and/or neural-net principles to generate a function of several functions in order to deal with still more complicated relationships among the cardiac variables, and to generate accordingly a criterion for cardiac arrhythmia-correcting electrical intervention.

Having thus described embodiments and features of the present invention, we note that it is a principal object of the present invention to employ as a criterion for cardiac arrhythmia-correcting electrical intervention, a particular value of a function of at least two cardiac variables.

A further object of the present invention is to employ as a criterion for cardiac arrhythmia-correcting electrical intervention, a particular value of a product of at least two cardiac variables.

A still further object of the present invention is to employ as a criterion for cardiac arrhythmia-correcting electrical intervention, a particular value of a product of at least two cardiac variables with a weight in the form of an exponent of a power associated with each variable.

Still another object of the present invention is to employ as a criterion for cardiac arrhythmia-correcting electrical intervention, a particular value of a sum of at least two cardiac variables.

A further object of the present invention is to employ as a criterion for cardiac arrhythmia-correcting electrical intervention, a particular value of a sum of at least two cardiac variables with a weight in the form of a multiplicative factor associated with each variable.

A still further object of the present invention is to employ as a criterion for cardiac arrhythmia-correcting electrical intervention, a particular value of a sum of at least two terms incorporating cardiac variables with weights in the form of an exponent of a power associated with each variable.

Yet a further object of the present invention is to employ a particular value of a function of multiple cardiac variables, such as various combinations of rate, onset, duration, correlations, absolute-amplitude ratio, stability, and physiological-variable values such as blood pressure and blood pH, to generate a criterion for cardiac arrhythmia-correcting electrical intervention.

A still further object of the present invention is the use of the neural-net principles to generate a function of several functions in order to deal with still more complicated relationships among the cardiac variables, and to generate accordingly a criterion for cardiac arrhythmia-correcting electrical intervention.

Yet a further object of the present invention is to employ fuzzy-logic principles that permit individual variables to change continuously through wide ranges for a given decision.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PRIOR ART

Figure 1A:
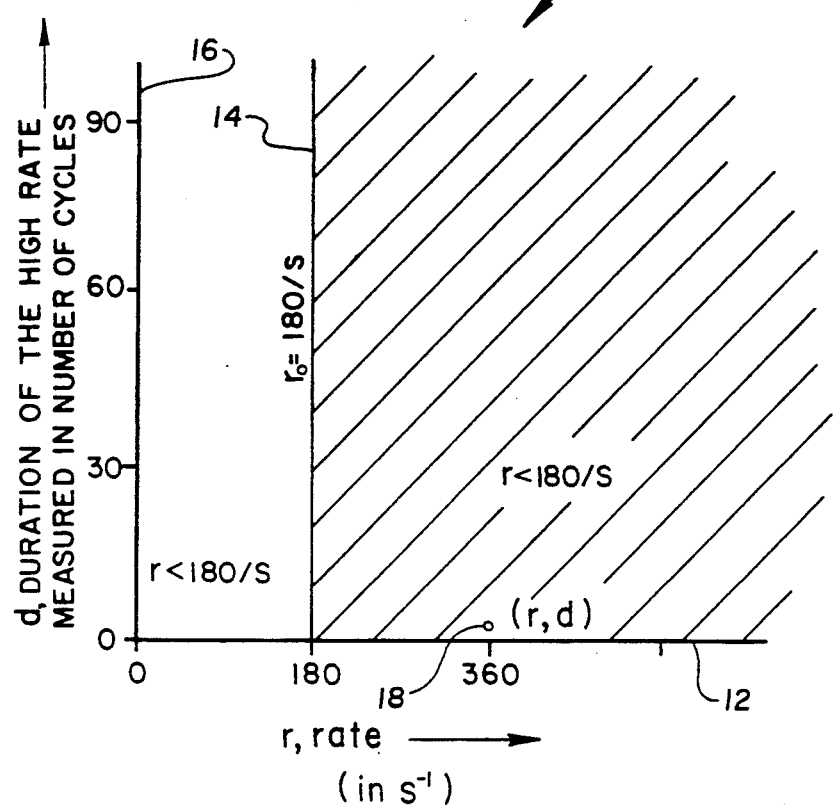
FIG. 1A illustrates a single-variable criterion for cardiac arrhythmia-correcting electrical intervention as employed in the prior art.

FIG. 1A illustrates a graph 10 having a single-variable criterion for cardiac arrhythmia-correcting electrical intervention as employed in the prior art, wherein the single variable, heart rate r, is presented on a scale 12 that also displays the threshold value 14 of r·=180/s above which intervention is ordered, and a second scale 16 that displays the duration d, measured in number of beats or cycles, of an episode of tachycardia, and that is used to relate this diagram to subsequent diagrams, and to illustrate the fact that a condition represented by the point 18 would trigger intervention in spite of the fact that the tachycardia is so fleeting that intervention is inappropriate.

Figure 1B:
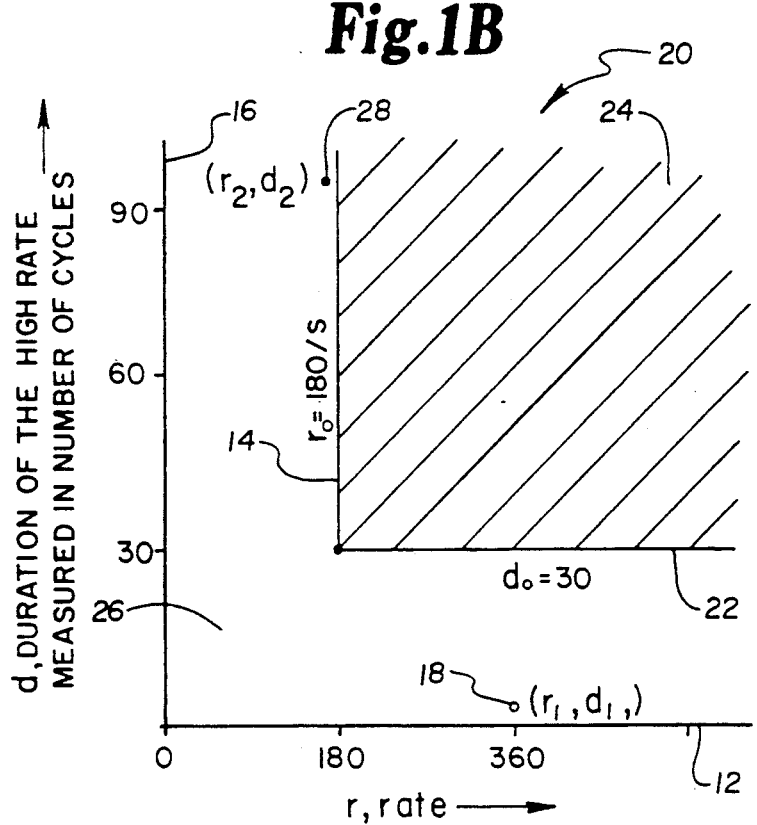
FIG. 1B illustrates a two-variable criterion for cardiac arrhythmia-correcting electrical intervention as employed in the prior art.

FIG. 1B illustrates a graph 20 having a two-variable criterion for cardiac arrhythmia-correcting electrical intervention as employed in the prior art, wherein the first variable, heart rate r, is presented on a scale 12 and which also displays the threshold value 14 of r·=180/s above which intervention is in order, and a second scale 16 which displays the second variable, the duration d, measured in number of beats or cycles, of an episode of tachycardia, and that also displays the threshold value 22 of d·=30 above which intervention is in order, with the lines 14 and 22 constituting the boundary between the shaded area 24 wherein intervention is in order and the unshaded area 26 wherein intervention is not in order. Thus, illustrated is the fact that a condition represented by the point 18 appropriately will not in this system trigger intervention, and to illustrate further the fact that a condition represented by the point 28 inappropriately will not trigger intervention in spite of the fact that rate is very close to the threshold 14 and duration is far greater than the threshold 22. All other numerals correspond to those elements previously described.

DESCRIPTION OF THE PREFERRED EMBODIMENTS

Figure 2A:
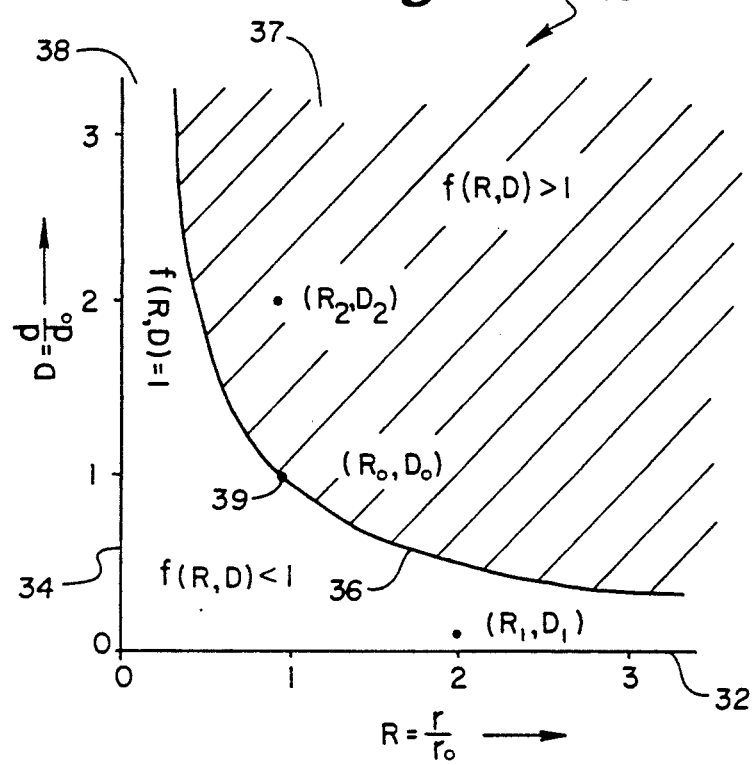
FIG. 2A illustrates a criterion of the present invention for cardiac arrhythmia-correcting electrical intervention, namely, a particular value of a product of at least two cardiac variables.

FIG. 2A illustrates a graph 30 having a criterion for cardiac arrhythmia-correcting electrical intervention as employed in the present invention wherein the first variable, normalized heart rate R, is presented on a first scale 32, and the second variable, the normalized duration D of an episode of tachycardia, is presented on a second scale 34. The function f(R, D) is in this example the product of R and D, and the criterion for intervention is a value of the function in excess of unity, with the curve 36 being the plot of the function for the value unity, and therefore constituting the boundary between the shaded area 37 wherein intervention is in order and the unshaded area 38 wherein intervention is not in order, and passing through the point 39 that represents the reference values R· and D·.

Figure 2B:
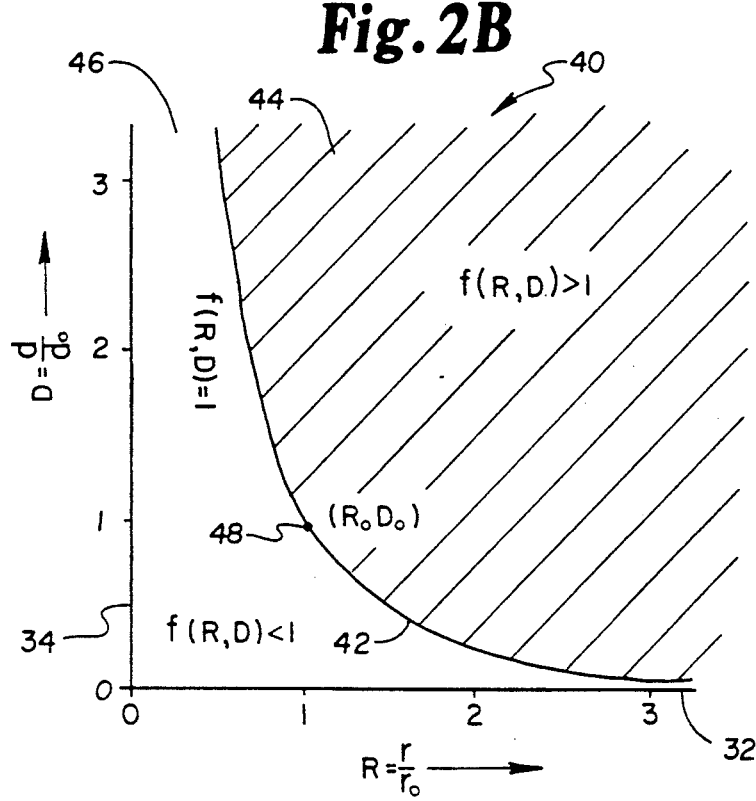
FIG. 2B illustrates a criterion of the present invention for cardiac arrhythmia-correcting electrical intervention, namely, particular value of a product of at least two cardiac variables, with a weighting exponent applied to each variable.

FIG. 2B illustrates a graph 40 displaying a criterion for cardiac arrhythmia-correcting electrical intervention as employed in the present invention wherein the first variable, normalized heart rate R, is presented on a first scale 32, and the second variable, the normalized duration D of an episode of tachycardia, is presented on a second scale 34 where all numerals correspond to those elements previously described. The function f(R, D) is in this example the product of R and D, but with R raised to the power of two for the purpose of weighting, and with D remaining at the power of one, and with the criterion for intervention being a value of the function in excess of unity, with the curve 42 being the plot of the function for the value unity, and therefore, constituting the boundary between the shaded area 44 wherein intervention is in order and the unshaded area 46 wherein intervention is not in order, and passing through the point 48 that represents the reference values R· and D· of the normalized variables R and D.

Figure 3A:
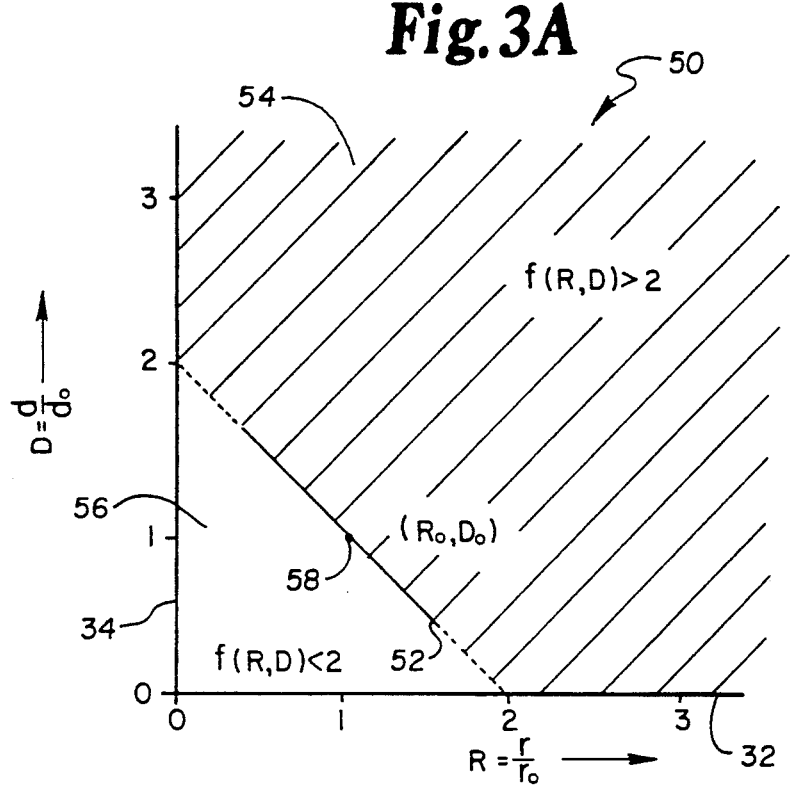
FIG. 3A illustrates a criterion of the present invention for cardiac arrhythmia-correcting intervention, namely, a particular value of the sum of at least two cardiac variables.

FIG. 3A illustrates a graph 50 displaying a criterion for cardiac arrhythmia-correcting electrical intervention as employed in the present invention wherein the first variable, normalized heart rate R, is presented on a first scale 32, and the second variable, the normalized duration D of an episode of tachycardia, is presented on a second scale 34 where all numerals correspond to those elements previously described. The function f(R, D) is in this example the sum of R and D, and the criterion for intervention is a value of the function in excess of two, with the curve 52 being the plot of the function for the value of two, and therefore constituting the boundary between the shaded area 54 wherein intervention is in order and the unshaded area 56 wherein intervention is not in order, and passing through the point 58 that represents the reference values R· and D· of the normalized variables R and D, and with the portions of the function near the axis deleted electronically by declaring a minimum value of each variable individually for a decision to intervene.

Figure 3B:
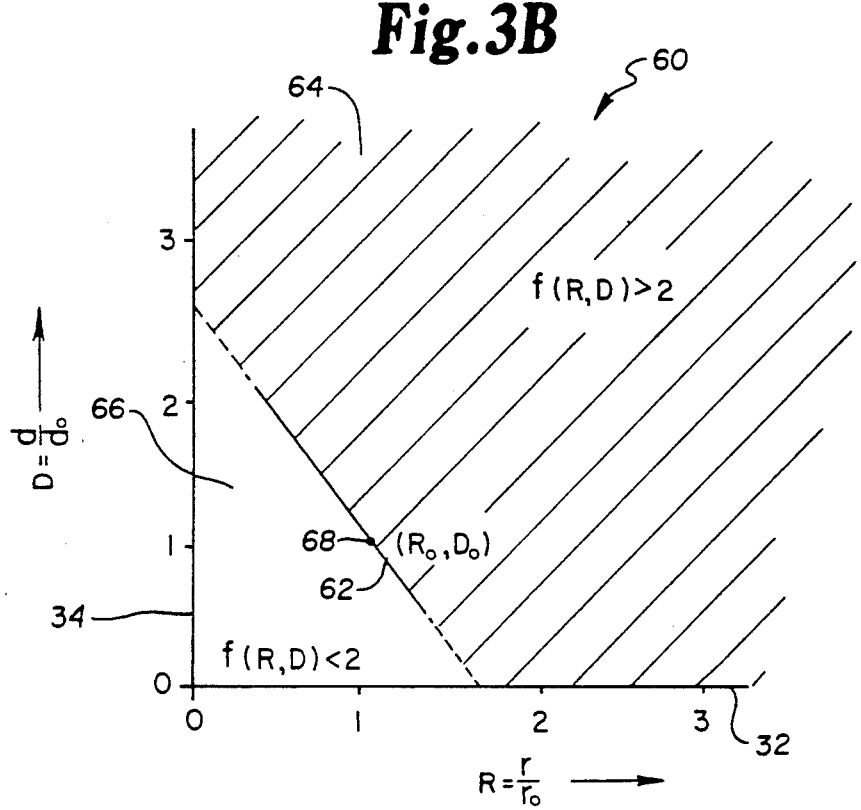
FIG. 3B illustrates a criterion of the present invention for cardiac arrhythmia-correcting electrical intervention that is a particular value of a sum of at least two cardiac variables with a weight in the form of a multiplicative factor associated with each variable.

FIG. 3B illustrates a graph 60 displaying a criterion for cardiac arrhythmia-correcting electrical intervention as employed in the present invention wherein the first variable, normalized heart rate R, is presented on a first scale 32, and the second variable, the normalized duration D of an episode of tachycardia, is presented on a second scale 34 where all numerals correspond to those elements previously described. The function f(R, D) is in this example the sum of R and D, with a weight in the form of the multiplicative factor 1.2 associated with R and the multiplicative factor 0.8 associated with D, and with the criterion for intervention being a value of the function in excess of two, with the curve 62 being the plot of the function for the value of two, and therefore constituting the boundary between the shaded area 64 wherein intervention is in order and the unshaded area 66 wherein intervention is not in order, and passing through the point 68 that represents the reference values R· and D· of the normalized variables R and D, and with the portions of the function near the axis deleted electronically by declaring a minimum value of each variable individually for a decision to intervene.

Figure 4A:
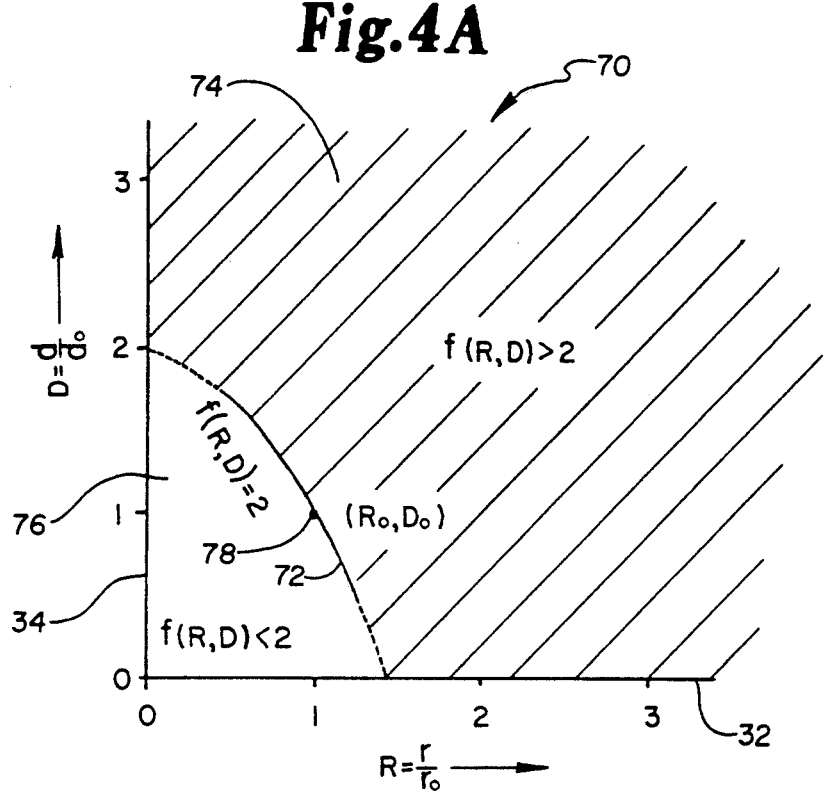
FIG. 4A illustrates a criterion of the present invention for cardiac arrhythmia-correcting electrical intervention, namely, a particular value of the sum of at least two cardiac variables, with a positive weighting exponent applied to each variable.

FIG. 4A illustrates a graph 70 displaying the criterion for cardiac arrhythmia-correcting electrical intervention as employed in the present invention wherein the first variable, normalized heart rate R, is presented on a first scale 32, and the second variable, the normalized duration D of an episode of tachycardia, is presented on a second scale 34 where all numerals correspond to those elements previously described. The function f(R, D) is in this example the sum of R and D, a particular value of the sum of at least two cardiac variables, with a positive weighting exponent 2 applied to R, and the positive weighting exponent 1 applied to D, and the criterion for intervention being a value of the function in excess of two, with the curve 72 being the plot of the function for the value of two, and therefore constituting the boundary between the shaded area 74 wherein intervention is in order and the unshaded area 76 wherein intervention is not in order, and passing through the point 78 that represents the reference values R· and D· of the normalized variables R and D, and with the portions of the function near the axis deleted electronically by declaring a minimum value of each variable individually for a decision to intervene.

Figure 4B:
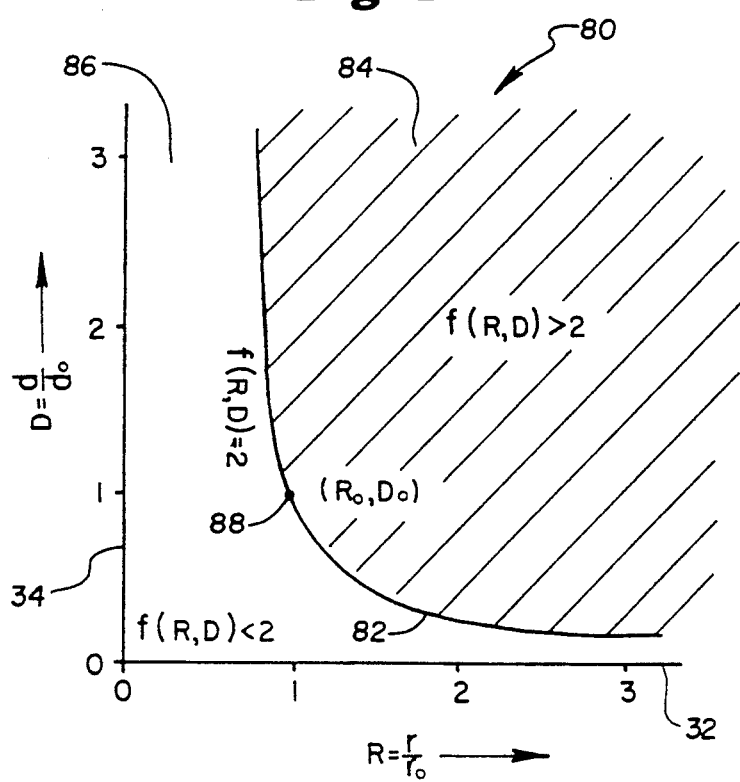
FIG. 4B illustrates a criterion of the present invention for cardiac arrhythmia-correcting electrical intervention, namely, a particular value of the sum of at least two cardiac variables, with a negative weighting exponent applied to each variable.

FIG. 4B illustrates a graph 80 displaying a criterion for cardiac arrhythmia-correcting electrical intervention as employed in the present invention wherein the first variable, normalized heart rate R, is presented on a first scale 32, and the second variable, the normalized duration D of an episode of tachycardia, is presented on a second scale 34 where all numerals correspond to those elements previously described. The function f(R, D) is in this example the sum of R and D, a particular value of the sum of at least two cardiac variables, with the negative weighting exponent −2 applied to R, and the negative weighting exponent −1 applied to D, and the criterion for intervention being a value of the function in excess of two, with the curve 82 being the plot of the function for the value of two, and therefore, constituting the boundary between the shaded area 84 wherein intervention is in order and the unshaded area 86 wherein intervention is not in order, and passing through the point 88 that represents the reference values R· and D· of the normalized variables R and D.

FIG. 5A illustrates a diagram 90 representing a circuit for generating a criterion for cardiac arrhythmia-correcting electrical intervention as employed in the present invention, wherein a single sensor 92 with three associated signal-processing circuits delivers digital information on cardiac rate, tachycardia duration, and cardiac-waveform amplitude into dedicated function generators 94a–94c, which are within the module 96, enclosed within the dashed line, and whose output signals are combined in the multivariable-function generator 98 that is also within the module 96 and that produces the prescribed function of the variables, so that a threshold discriminator 100 that follows the module 96 can deliver a positive or negative output 102, depending on whether the threshold is exceeded or not.

Figure 5B:
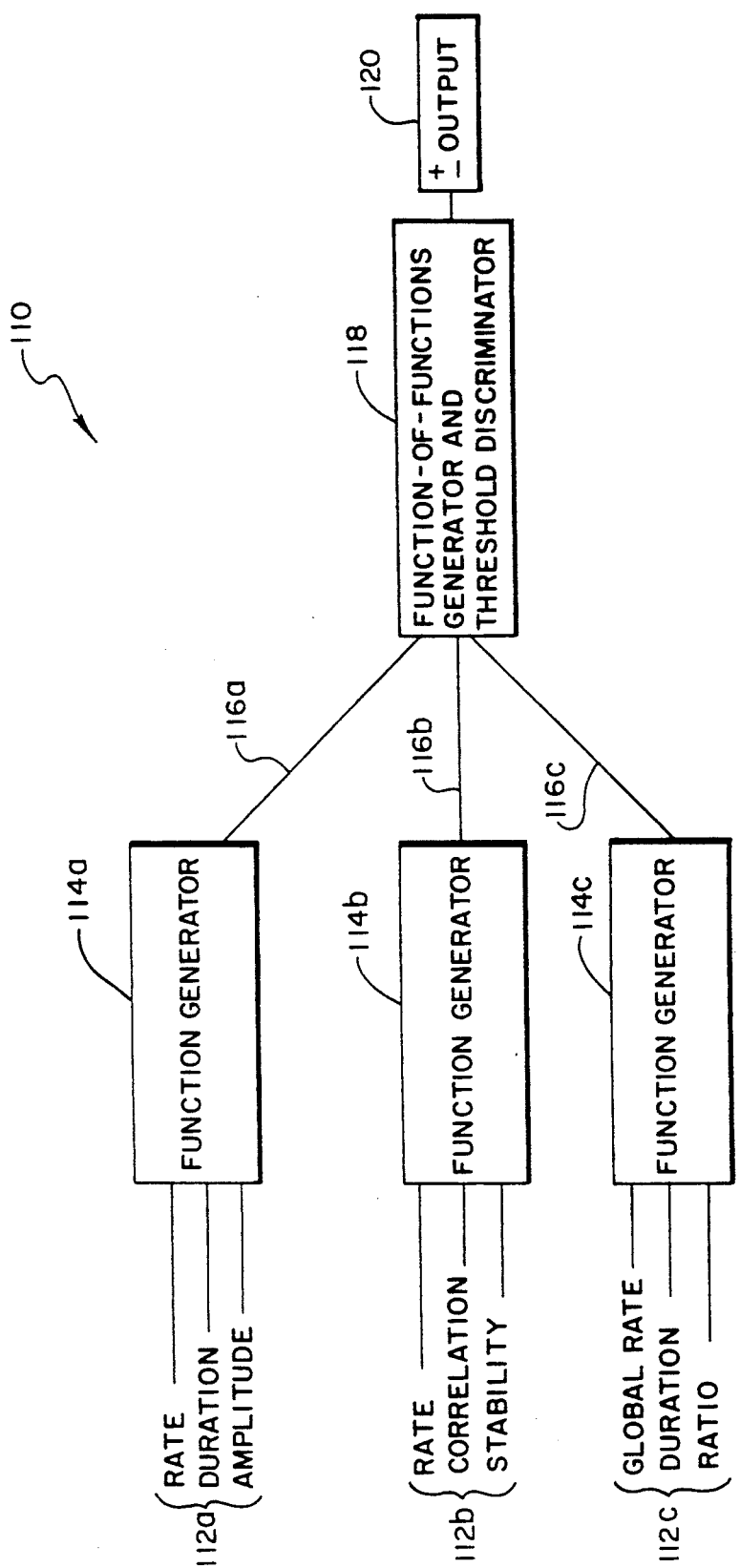
FIG. 5A illustrates a circuit module of the present invention for cardiac arrhythmia-correcting electrical intervention, into which in this example, information from a single sensor is fed into three different associated signal-processing circuits, each of which produces a digital signal characterizing a different feature of cardiac performance, with each resulting signal fed into a different function generator, where outputs in turn are combined in another function generator that produces the prescribed function of the variables, so that a threshold discriminator can deliver a positive or negative output, depending on whether the threshold is exceeded or not; and, FIG. 5B illustrates a neural network of the present invention for cardiac arrhythmia-correcting electrical intervention with, in this example, three cardiac variables fed into each of three modules, each similar to that enclosed in the dashed line of FIG. 5A, and from which the three output signals are sent to a function-of-functions generator that also performs threshold discrimination, so that the neural net can deliver a positive or negative output, depending on whether the threshold is exceeded or not.

FIG. 5B illustrates a neural network 110 of the present invention for generating a criterion for cardiac arrhythmia-correcting electrical intervention with, in this example, three cardiac-variable sets 112a–112c fed into each of three function generators 114a–114c, each similar to the module 96 enclosed in the dashed line in FIG. 5A, and from which the three output signals 116a–116c are sent to a function-of-functions generator 118 that also performs threshold discrimination, so that the neural net 110 can deliver a positive or negative output 120, depending on whether the threshold is exceeded or not.

MODE OF OPERATION

A major shortcoming in the prior art for detecting cardiac arrhythmias for the purpose of making an electrical intervention decision has been that each variable sensed was given in effect a "veto" over intervention on the basis of its own particular predetermined threshold value, and irrespective of the values of companion variables. The present invention overcomes this problem by generating a function of relevant variables, and assigning a threshold value to the function. As a result, an individual variable can range widely for a positive intervention decision, depending upon the values of the companion variables. Thus, the invention exploits features often described as those associated with fuzzy logic.

The function chosen for this purpose can be as simple or as complicated as one desires, with the choice depending upon the current state of advancing knowledge. Even further flexibility can be achieved by employing the principles of the neural net, wherein functional values can themselves be combined, with another threshold value assigned to the result of that combination, and so on.

The present invention relates generally to detection methods for cardiac arrhythmias, and more particularly to methods of improved accuracy for identifying the presence of conditions that can be ameliorated by antitachycardia pacing, or by cardioversion shock, or by defibrillation shock.

Among the cardiac variables that can be sensed for purposes of the present invention are heart rate, rate acceleration, duration of the high heart rate, the correlation between electrical pulses and separate signals derived from a mechanical sensor of some description, and between local and global electrical signals, the ratio of the average absolute value of the signal voltage to the peak absolute voltage, signal amplitude, and physiological variables such as blood pressure and blood pH.

Various modifications can be made to the present invention without departing from the apparent scope hereof.

We claim:

1. An improved arrhythmia-detection criteria process for detecting a tachycardia/fibrillation cardiac arrhythmia in a human patient by a cardioverter defibrillator device connected to at least two implanted electrodes located in the human patient that can selectively deliver cardioversion/defibrillation cardiac arrhythmia-correcting electrical intervention therapy comprised of one or more electrical pulses of greater than about 0.1 Joules, the process including the device-implemented steps of: (a) continually receiving a plurality of cardiac variables representing sensed values in the human patient, (b) evaluating the plurality of cardiac variables to determine whether a tachycardia/ fibrillation cardiac arrhythmia is present, and (c) if such an arrhythmia is present, determining an appropriate therapy to be delivered to treat the arrhythmia, the improvement comprising the device-implemented sub-steps of follows:

(b1) using one or more chosen mathematical algebraic functions relating two or more of the cardiac variables to generate a threshold criterion that is at least a threshold curve; and (b2) using the threshold curve to define a boundary above which a tachycardia/fibrillation cardiac arrhythmia is deemed to be present.

2. The process of claim 1 wherein the chosen function is the product of at least two cardiac variables.

3. The process of claim 1 wherein the chosen function is a product of at least two cardiac variables with a weight in the form of an exponent of a power associated with each variable.

4. The process of claim 1 wherein the chosen function is the sum of at least two cardiac variables.

5. The process of claim 1 wherein the chosen function is the sum of at least two cardiac variables with a weight in the form of a multiplicative factor associated with each variable.

6. The process of claim 1 wherein the chosen function is the sum of at least two cardiac variables with a weight in the form of an exponent of a power associated with each variable.

7. The process of claim 1 wherein the chosen function is the sum of at least two cardiac variables with weights in the form of a multiplicative factor associated with each variable and additional weights in the form of exponents of a power associated with each variable.

8. The process of claim 1 wherein the cardiac variables employed include at least one of these variables: rate, onset, duration, correlations, absolute-amplitude ratio, stability; and the physiological-variables blood pressure and blood pH.

9. The process of claim 1 wherein two or more mathematical algebraic functions are used in step (b1) and neural-net principles are used to generate at least one of the two or more mathematical algebraic functions.

10. An improved arrhythmia-detection criteria process for detecting a tachycardia/fibrillation cardiac arrhythmia in a human patient by a cardioverter defibrillator device connected to at least two implanted electrodes located in the human patient that can selectively deliver cardioversion/defibrillation cardiac arrhythmia-correcting electrical intervention therapy comprised of one or more electrical pulses of greater than about 0.1 Joules, the process including the device-implemented steps of: (a) continually receiving a plurality of cardiac variables representing sensed values in the human patient, (b) evaluating the plurality of cardiac variables to determine whether a tachycardia/fibrillation cardiac arrhythmia is present, and (c) if such an arrhythmia is present, determining an appropriate therapy to be delivered to treat the arrhythmia, the improvement comprising the device-implemented sub-steps as follows:

(b1) selecting an explicit and well-defined threshold intervention criteria which is at least a threshold curve defined by one or more mathematical algebraic functions relating two or more of the cardiac variables;

(b2) using the threshold curve to define a boundary above which a tachycardia/fibrillation cardiac arrhythmia is deemed to be present by permitting individual cardiac variables to vary within wide limits at threshold conditions, depending upon the values of companion variables.

11. An improved arrhythmia-detection criteria process for detecting a tachycardia/fibrillation cardiac arrhythmia in a human patient by a cardioverter defibrillator device connected to at least two implanted electrodes located in the human patient that can selectively deliver cardioversion/defibrillation cardiac arrhythmia-correcting electrical intervention therapy comprised of one or more electrical pulses of greater than about 0.1 Joules, the process including the device-implemented steps of: (a) continually receiving a plurality of cardiac variables representing sensed values in the human patient, (b) evaluating the plurality of cardiac variables to determine whether a tachycardia/fibrillation cardiac arrhythmia is present, and (c) if such an arrhythmia is present, determining an appropriate therapy to be delivered to treat the arrhythmia, the improvement comprising the device-implemented sub-steps as follows:

(b1) using two or more functions, each function relating two or more of the cardiac variables, to generate a threshold criterion; and (b2) combining the threshold criterion generated in step (b1) by using a mathematical algebraic function that relates the threshold criterion in terms of inputs to a neural-network, an output of which defines a boundary above which a tachycardia/fibrillation cardiac arrhythmia is deemed to be present.

12. The process of claim 11 wherein one or more of the functions of step (b1) are mathematical algebraic functions.

13. The process of claim 11 wherein one or more of the functions of step (b1) are implemented as a neural-network.

14. The process of claim 11 wherein the neural-network is implemented in software in a processor within the device.

15. The process of claim 11 wherein the neural-network is implemented in hardware circuitry within the device.

16. An improved arrhythmia-detection criteria process for detecting a tachycardia/fibrillation cardiac arrhythmia in a human patient by a cardioverter defibrillator device connected to at least two implanted electrodes located in the human patient that can selectively delivery cardioversion/defibrillation cardiac arrhythmia-correcting electrical intervention therapy comprised of one or more electrical pulses of greater than about 0.1 Joules, the process including the device-implemented steps of: (a) continually receiving a plurality of cardiac variables representing senses values in the human patient, (b) evaluating the plurality of cardiac variables to determine whether a tachycardia/fibrillation cardiac arrhythmia is present, and (c) if such an arrhythmia is present, determining an appropriate therapy to be delivered to treat the arrhythmia, the improvement comprising the device-implemented sub-steps as follows:

(b1) using one or more mathematical algebraic functions, each function relating two or more of the cardiac variables and being implemented as a neural network, to generate at least a threshold curve; and (b2) using the threshold curve to define a boundary above which a tachycardia/fibrillation cardiac arrhythmia is deemed to be present.

17. The process of claim 16 wherein at least one neural-network is implemented in software in a processor within the device.

18. The process of claim 16 wherein at least one neural-network is implemented in hardware circuitry within the device.

* * * * *